(12) United States Patent
Mackin

(10) Patent No.: US 7,942,813 B2
(45) Date of Patent: *May 17, 2011

(54) DETACHABLE ENDOTRACHEAL CAMERA

(76) Inventor: Robert A. Mackin, Flagstaff, AZ (US)

( * ) Notice: Subject to any disclaimer, the term of this patent is extended or adjusted under 35 U.S.C. 154(b) by 610 days.

This patent is subject to a terminal disclaimer.

(21) Appl. No.: 11/865,256

(22) Filed: Oct. 1, 2007

(65) Prior Publication Data

US 2008/0021273 A1   Jan. 24, 2008

Related U.S. Application Data

(62) Division of application No. 10/775,904, filed on Feb. 10, 2004, now Pat. No. 7,297,105.

(51) Int. Cl.
*A61B 1/267*   (2006.01)
*A61B 1/07*   (2006.01)

(52) U.S. Cl. ........ 600/120; 600/112; 600/160; 600/178; 600/182

(58) Field of Classification Search .............. 600/109, 600/112, 120, 160, 178, 182; 348/73; 128/200.26, 128/207.14

See application file for complete search history.

(56) References Cited

U.S. PATENT DOCUMENTS

| | | | |
|---|---|---|---|
| 3,788,304 A | 1/1974 | Takahashi | 600/141 |
| 4,784,133 A | 11/1988 | Mackin | 128/303.1 |
| 4,846,153 A | 7/1989 | Berci | 600/109 |
| 4,961,738 A | 10/1990 | Mackin | 606/15 |
| 4,976,710 A | 12/1990 | Mackin | 606/15 |
| 5,285,778 A | 2/1994 | Mackin | 28/207.15 |
| 5,323,767 A | 6/1994 | Lafferty et al. | 600/109 |
| 5,400,771 A | 3/1995 | Pirak et al. | 600/109 |
| 6,193,763 B1 | 2/2001 | Mackin | 624/427 |
| 6,322,498 B1 | 11/2001 | Gravenstein et al. | 600/120 |
| 6,408,203 B2 | 6/2002 | Mackin | 600/433 |
| 6,554,765 B1 | 4/2003 | Yarush et al. | 600/132 |
| 6,692,431 B2 * | 2/2004 | Kazakevich | 600/178 |
| 6,761,561 B2 | 7/2004 | Mandelkern et al. | 433/29 |
| 6,902,529 B2 | 6/2005 | Onishi et al. | 600/118 |
| 6,929,600 B2 | 8/2005 | Hill | 600/120 |
| 2002/0022763 A1 | 2/2002 | Sano et al. | 600/109 |
| 2002/0137984 A1 | 9/2002 | Chhibber et al. | 600/120 |
| 2003/0012461 A1 | 1/2003 | Satoh et al. | 382/325 |
| 2004/0133073 A1 | 7/2004 | Berci et al. | 600/112 |
| 2004/0147809 A1 | 7/2004 | Kazakevich | 600/178 |

* cited by examiner

*Primary Examiner* — John P Leubecker
(74) *Attorney, Agent, or Firm* — The von Hellens Law Firm, Ltd.

(57) ABSTRACT

A low cost camera and radio frequency transmitter are detachably coupled to an endotracheal tube to obtain an image in real time of tissue at the distal end of the endotracheal tube. The image recorded by the camera is transmitted to a low cost radio frequency receiver nearby and conveyed to a video monitor to display the image. The use of a wireless transmission system avoids the presence of wires and cords that otherwise might become entangled and cause the endotracheal tube to be inadvertently repositioned or pulled out of the patient.

12 Claims, 2 Drawing Sheets

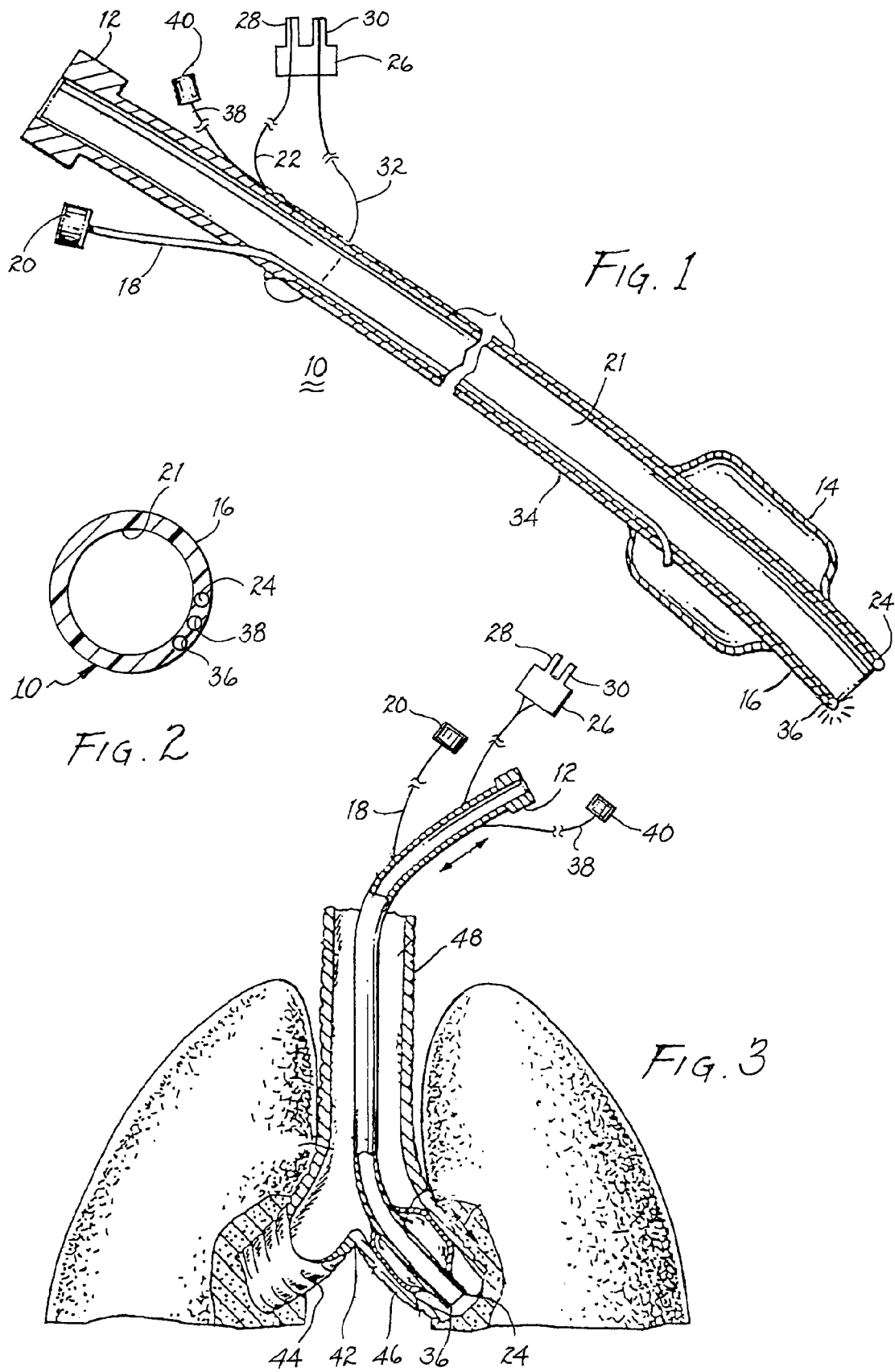

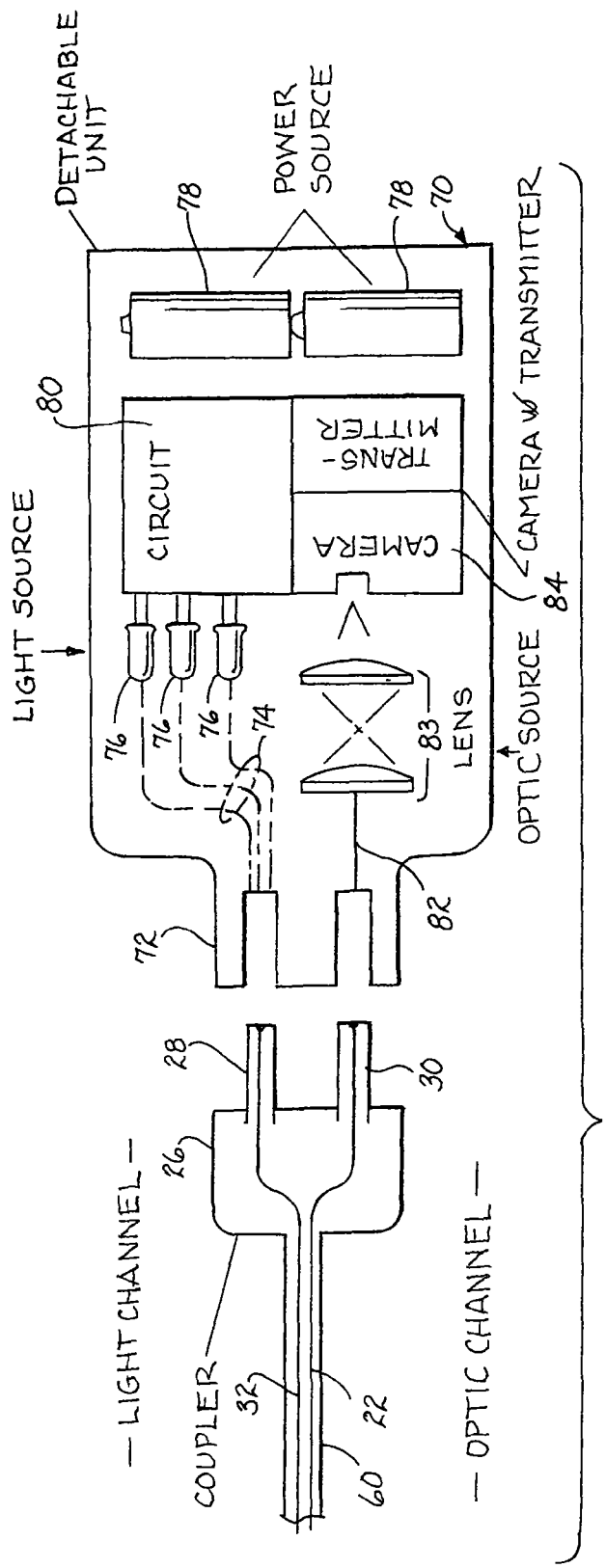
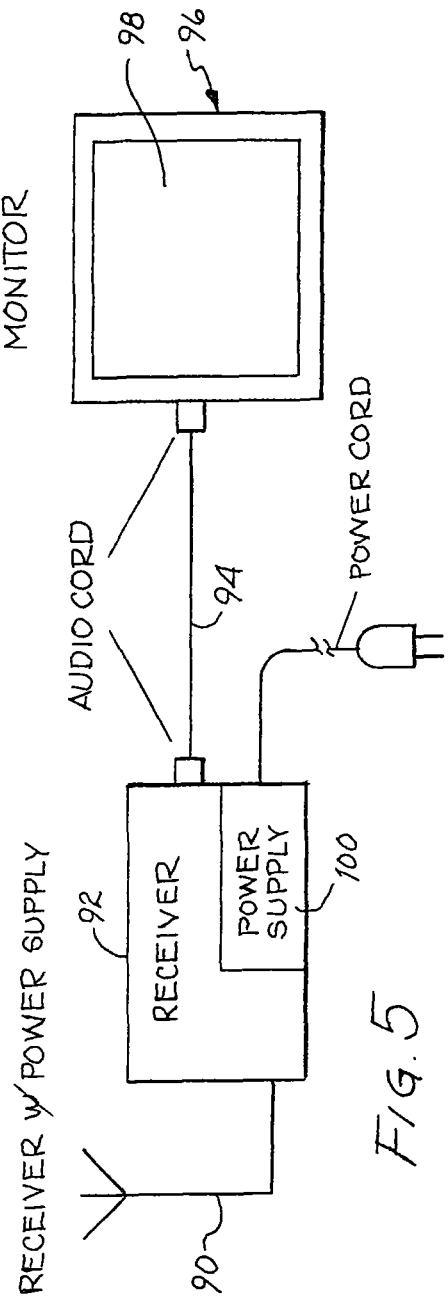
Fig. 4
Fig. 5

DETACHABLE ENDOTRACHEAL CAMERA

CROSS REFERENCE TO RELATED APPLICATIONS

This application is a divisional for patent application entitled "Endotracheal Camera" filed Feb. 10, 2004 and assigned Ser. No. 10/775,904, now U.S. Pat. No. 7,297,105, and describing an invention by the present inventor.

BACKGROUND OF THE INVENTION

The present invention relaters to endotracheal tubes and, more particularly, to an endotracheal tube having an illuminator at its distal end and coupled with detachably attached camera for wireless transmission of an image to a receiver for display on a video monitor.

The basic tenets attendant endotracheal tubes having an illuminator at the distal end are illustrated and described in U.S. Pat. No. 5,285,778 and relating to an invention by the present inventor; which patent is incorporated herein by reference. The endotracheal tube described therein includes an optical fiber extending through the endotracheal tube to a viewing lens at the distal end of the tube. An eye piece is attached to the proximal end of the optical fiber to permit viewing through the lens. Illumination of the area under inspection is provided by a high intensity light source extending via the endotracheal tube to an illumination port at the distal end.

An endotracheal tube so modified permits the physician to view in real time the tissue being inspected. However, an image or picture cannot be obtained for inspection and analysis at a later date.

SUMMARY OF THE INVENTION

In the present invention, the eye piece of the tracheal tube disclosed in U.S. Pat. No. 5,285,778 is replaced by a connector in operative engagement with a fiber optic bundle extending from the lens at the distal end of the endotracheal tube and with a fiber optic bundle for conveying light to an illumination port also at the distal end of the endotracheal tube. A camera and transmitter assembly of miniature size is coupled to the connector to provide power to the illumination port and to record the image transmitted through the fiber optic bundle from the lens. A signal conveying the images recorded is transmitted by the transmitter to a nearby receiver. The receiver manipulates the signal received and provides a real time display of the images on a video monitor.

It is therefore a primary object of the present invention to provide a method for viewing tissue at the distal end of an endotracheal tube on a real time monitor with a wireless transmitter and receiver.

Another object of the present invention is to provide an inexpensive camera for recording an image at the distal end of an endotracheal tube.

A yet further object of the present invention is to provide a low power transmitter coupled with a camera to transmit an image recorded by the camera at the distal end of an endotracheal tube to a receiver for viewing the image on a video monitor.

Still another object of the present invention is to provide a low power transmitter and receiver for transmitting an image at the distal end of an endotracheal tube to a video monitor for real time viewing.

A further object of the present invention is to provide a small sized inexpensive camera and transmitter detachably attachable to a connector coupled with an endotracheal tube to transmit to a receiver an image from the distal end of the endotracheal tube.

A yet further object of the present invention is to provide a wireless transmission to a video monitor coupled with a camera recording an image at the distal end of an endotracheal tube using a low power radio frequency transmitter and receiver.

A still further object of the present invention is to provide a method for displaying an image real time on a video monitor by capturing the image to be displayed with a camera coupled to the distal end of an endotracheal tube and transmitting the image by a radio frequency transmitter to a corresponding receiver to produce a signal for the video monitor.

A still further object of the present invention is to provide a method for viewing on a video monitor in real time an image at the distal end of an endotracheal tube using essentially off the shelf low cost camera and a wireless transmitter and receiver.

These and other objects of the present invention will become apparent to those skilled in the art as the description there proceeds.

BRIEF DESCRIPTION OF THE DRAWINGS

The present invention will be described with greater specificity and clarity with reference to the following drawings, in which:

FIG. 1 is a partial cross sectional view of an endotracheal tube embodying aspects of the present invention;

FIG. 2 is a partial cross section of the endotracheal tube;

FIG. 3 is a partial cross sectional view illustrating placement within a patient of an endotracheal tube;

FIG. 4 illustrates a camera and a transmitter for attachment with a connector of an endotracheal tube; and FIG. 5 illustrates a receiver and an attached video monitor.

DESCRIPTION OF THE PREFERRED EMBODIMENT

Referring to FIG. 1, there is shown an endotracheal tube 10 having a connector 12 for connection to a conventional ventilator to assist a patient's breathing function. The endotracheal tube includes an inflatable balloon 14 in proximity to its distal end 16. The inflatable balloon is inflated by a tube 18 connected through a connector 20 to a small syringe-like air pump after the endotracheal tube has been inserted into a patient's trachea.

Prior endotracheal tubes do not permit any visualization of a patient's tracheal and bronchial passages. If such visualization is needed, connector 12 is disconnected from the ventilator and a conventional bronchoscope is inserted down through hollow passage 21 of the endotracheal tube to allow a physician to determine if a lot of mucus is present in either lung or in either of the left or right stem main bronchi. If it is necessary to suction mucus out of either of the patient's lungs, a suctioning tube is inserted through hollow passage 21. The endotracheal tube may have to be disconnected from the ventilator to allow visualization in the trachea of the lungs or to allow suctioning of the mucus, blood, etc., if the endotracheal tube does not have a sealable side port through which the suctioning tube can be inserted.

When a skilled physician, often a pulmonologist, inserts an endotracheal tube into a patient, it would be desirable for a nurse to be able to easily monitor the position of the endotracheal tube in a patient's trachea to determine if its location has been shifted. If so, the nurse would know whether to call a physician to reposition the tracheal tube. It would also be desirable to determine accurately the position of the tracheal tube without requiring an x-ray of the patient.

Still referring to FIG. 1, endotracheal tube 10 includes an optical fiber, hereinafter referred to as fiber optic bundle 22, that extends through the tracheal tube to a viewing lens 24 at distal end 16. The fiber optic bundle can be an inexpensive plastic optical fiber costing only a few dollars and embedded in the wall of the tracheal tube. The fiber optic bundle is operatively connected to a connector 26 which includes two prongs 28, 30 of which prong 28 carries the fiber optic bundle. A second plastic optical fiber, hereinafter referred to as fiber optic bundle 32, extends through wall 34 of endotracheal tube 10 to an illumination port 36 at distal end 16.

FIG. 2 is a view of the distal end of tracheal tube 10. A hollow tube 38 extends from a flushing inlet port connector 40 (see FIG. 1) and extends through the endotracheal tube so that a transparent saline flushing liquid can be forced through the tube to wash mucus away from viewing lens 24 and illumination port 36. Such mucus may collect thereon during insertion of the tracheal tube into the patient's trachea or afterward.

One major advantage of endotracheal tube 10 is that the carina (a cartilaginous structure) 42 (see FIG. 3) can be easily viewed during insertion of the endotracheal tube so that a nurse or a physician can readily determine how far into the patient's trachea to properly insert the endotracheal tube. This avoids the need for an x-ray process to determine if the endotracheal tube is properly inserted. As the endotracheal tube can become malpositioned in the patient and which would normally require a later x-ray to check for proper placement, direct visualization afforded by the present invention can avoid the need for such a repeat x-ray. Another advantage is that the nurse or physician can easily view the conditions in branches 44, 46 of trachea 48 to determine the presence of mucus or other condition and to determine whether there is a need for immediate suctioning of mucus, blood, etc., from either lung or the passages thereto.

Referring to FIG. 4, there is shown a male connector 26 having prongs 28, 30 extending therefrom. Fiber optic bundle 32 is in functional and operative engagement with prong 28 to transmit light from the end of the prong to illumination port 36 at distal end 16 of the endotracheal tube. Fiber optic bundle 22 is coupled with lens 24 at the distal end of the endotracheal tube to transmit light, that is an image, to the end of prong 30. As illustrated, fiber optic bundles 22 and 32 may be incased within a sheath 60.

A removable module 70 includes a female connector 72 for receiving prongs 28, 30 of connector 26. Upon mating of connectors 26, 72, fiber optic bundle 32 within prong 28 is placed in communication with fiber optic bundle 74, the latter being in communication with and receiving light from light emitting diodes 76. Electrical power for the light emitting diodes is provided by circuit 80 connected to batteries 78. Prong 30 of male connector 26 mates with female connector 72 to transmit light, that is, the image visible through lens 24 (see endotracheal tube 10) to convey the received light through a further fiber optic bundle 82 to a lens system 83. The lens system is interconnected with a small sized and relatively inexpensive electronic camera 84. Cameras suitable for this purpose cost less than $100.00 and can be found for less than $50.00 from commercial outlets. The camera is interconnected with a low power radio frequency transmitter 86 to transmit the images recorded by the camera. Transmitters of this type are readily available for less than $100.00 and may be found for less than $50.00 from commercial outlets.

As shown in FIG. 5, an antenna 90 is connected to a radio frequency receiver 92 and receives the images detected by camera 84 and transmitted by transmitter 86. The received image is conveyed via an electrical conductor or cord 94 to a video monitor 96. The video monitor includes a screen 98 for displaying the image recorded by camera 84. As illustrated, a power supply provides power to receiver 92 and to video monitor 96 through an electrical conductor 102. Power to the power supply may be provided by a conventional plug 104 for engagement with a conventional wall socket.

In summary, the image conveyed from the lens at the distal end of the endotracheal tube is digitalized and recorded by a camera. The image recorded by the camera is displayed real time on a video monitor through a wireless interconnection. The ease of a wireless transmission system in the confines of an operatory avoids the likelihood of a patient and an attending health care provider from becoming entangled with cords and wires.

Moreover, presently used wires and cables extending to a video monitor creates a hazard of an attending health care provider inadvertently interfering with such wires and/or cables and causing repositioning or pulling our of the endotracheal tube. This hazard is completely avoided by the present invention due to the absence of such wires and/or cables.

I claim:

1. Apparatus for displaying an image of tissue proximate the distal end of an endotracheal tube, said apparatus comprising in combination:
    a) an illumination port disposed at the distal end of the endotracheal tube for illuminating the tissue to be imaged;
    b) a fiber optic bundle for conveying light from a source of light to a connector;
    c) a further fiber optic bundle extending from said connector to said illumination port for conveying light to the tissue to be imaged;
    d) a lens disposed at the distal end of said endotracheal tube for receiving the image of the tissue;
    e) a yet further fiber optic bundle interconnecting said lens with said connector for conveying the image of tissue;
    f) a camera for recording the image conveyed by said yet further fiber optic bundle and including a still further fiber optic bundle interconnecting said connector with said camera to convey the image to said camera;
    g) a wireless transmitter for receiving the image from said camera and for transmitting the image;
    h) a wireless receiver for receiving the transmitted image; and
    i) a display for displaying the image received by said receiver.

2. The apparatus as set forth in claim 1 including batteries for providing power to said camera, to said source of light and to said transmitter.

3. The apparatus as set forth in claim 2 wherein said camera, said transmitter, said batteries and said source of light comprise a modular unit and wherein said connector provides engagement and disengagement of said modular unit with said further fiber optic bundle and said yet further fiber optic bundle.

4. The apparatus as set forth in claim 3 wherein said modular unit is portable such that a physician can manually manipulate said modular unit.

5. The apparatus as set forth in claim 1 wherein said source of light comprises at least one light emitting diode.

6. The apparatus as set forth in claim 5 wherein the terminal ends of said further fiber optic bundle and said yet further fiber optic bundle from said illumination port and from said lens, respectively, are secured to a first plug of said connector and including a second plug of said connector coupled with said camera and said source of light for disengageably engaging said first plug.

7. The apparatus as set forth in claim 6 including batteries for providing power to said camera and to said transmitter.

8. Apparatus for displaying an image of tissue proximate the distal end of an endotracheal tube, said apparatus comprising in combination:
   a) an illumination port disposed at the distal end of said endotracheal tube for illuminating the tissue to be imaged;
   b) a fiber optic bundle interconnecting said illumination port with a first prong of a connector;
   c) a lens for receiving an image of the tissue;
   d) a further fiber optic bundle interconnecting said lens with a second prong of said connector;
   e) a source of light, the light from said source of light being conveyed through said first prong and said fiber optic bundle to said illumination port;
   f) a low cost camera for recording the image and including a still further fiber optic bundle interconnecting said second prong with said camera to convey the image conveyed by said further fiber optic bundle to said camera;
   g) a low cost radio frequency transmitter for receiving the image from said camera and for transmitting the image;
   h) a low cost radio frequency receiver for receiving the image; and
   i) a video monitor for displaying the image received by said receiver.

9. The apparatus as set forth in claim 8 wherein said source of light comprises at least one light emitting diode.

10. The apparatus as set forth in claim 9 wherein said fiber optic bundle and said further fiber optic bundle are embedded in a wall of the endotracheal tube.

11. The apparatus as set forth in claim 8 wherein said source of light comprises at least one light emitting diode.

12. The apparatus as set forth in claim 8 wherein said fiber optic bundle and said further fiber optic bundle are embedded in a wall of the endotracheal tube.

* * * * *